(12) United States Patent
Liu et al.

(10) Patent No.: US 6,368,620 B2
(45) Date of Patent: **\*Apr. 9, 2002**

(54) FORMULATIONS COMPRISING LIPID-REGULATING AGENTS

(75) Inventors: Rong Liu, Gurnee; Qinghai Pan, Lake Bluff; Dennis Lee, Highland Park, all of IL (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/330,588

(22) Filed: Jun. 11, 1999

(51) Int. Cl.[7] ............................ A61K 9/48; A61K 9/64; A61K 9/14

(52) U.S. Cl. ................. 424/451; 424/456; 424/489; 424/490

(58) Field of Search ................. 424/451, 456, 424/489, 490

(56) References Cited

U.S. PATENT DOCUMENTS

| | | | | |
|---|---|---|---|---|
| 5,545,423 A | * | 8/1996 | Soon-Shiong et al. | 424/484 |
| 5,545,628 A | * | 8/1996 | Deboeck et al. | 514/49 |
| 5,766,637 A | * | 6/1998 | Shine et al. | 424/497 |
| 5,776,486 A | * | 7/1998 | Castor et al. | 424/450 |
| 6,074,670 A | | 6/2000 | Stamm et al. | |

OTHER PUBLICATIONS

Microparticulate Systems for the Delivery of Proteins and Vaccines, Ch. 3, Knutson et al., Prepartion of Microparticulates Using Supercritical Fluids, pp. 89–125 (Marcel Decker, Inc. 1996).*

Pharmaceutical Dosage Forms and Drug Delivery Systems, pp. 220–221 (Williams & Wilkins 1995).*

* cited by examiner

*Primary Examiner*—Thurman K. Page
*Assistant Examiner*—S. Howard
(74) *Attorney, Agent, or Firm*—Rockey, Milnamow & Katz, Ltd.

(57) ABSTRACT

The present invention is directed to a process for preparing a formulation comprising a lipid-regulating agent dissolved in a supercritical fluid, spraying the solution through a nozzle to form small particles of the lipid-regulating agent, forming a suspension of the particles of said lipid-regulating agent in a liquid, and collecting the particles.

9 Claims, 1 Drawing Sheet

FORMULATIONS COMPRISING LIPID-REGULATING AGENTS

FIELD OF THE INVENTION

The present invention relates to novel formulations comprising lipid-regulating agents.

BACKGROUND OF THE INVENTION

2-[4-(4-chlorobenzoyl)phenoxy]-2-methyl-propanoic acid, 1-methylethylester, also known as fenofibrate, is representative of a broad class of compounds having pharmaceutical utility as lipid regulating agents. More specifically, this compound is part of a lipid-regulating agent class of compounds commonly known as fibrates, and is disclosed in U.S. Pat. No. 4,058,552.

Fenofibrate has been prepared in several different formulations, c.f., U.S. Pat. Nos. 4,800,079 and 4,895,726. U.S. Pat. No. 4,895,726 discloses a co-micronized formulation of fenofibrate and a solid surfactant.

U.S. Pat. No. 4,961,890 discloses a process for preparing a controlled release formulation containing fenofibrate in an intermediate layer in the form of crystalline microparticles included within pores of an inert matrix. The formulation is prepared by a process involving the sequential steps of dampening said inert core with a solution based on said binder, then projecting said fenofibrate microparticles in a single layer onto said dampened core, and thereafter drying, before said solution based on said binder dissolves said fenofibrate microparticles, and repeating said three steps in sequence until said intermediate layer is formed.

European Patent Application No. EP0793958A2 discloses a process for producing a fenofibrate solid dosage form utilizing fenofibrate, a surface active agent and polyvinyl pyrrolidone in which the fenofibrate particles are mixed with a polyvinyl pyrrolidone solution. The thus obtained mixture is granulated with an aqueous solution of one or more surface active agents, and the granulate thus produced is dried.

PCT Publication No. WO 82/01649 discloses a fenofibrate formulation having granules that are comprised of a neutral core that is a mixture of saccharose and starch. The neutral core is covered with a first layer of fenofibrate, admixed with an excipient and with a second microporous outer layer of an edible polymer.

U.S. Pat. No. 5,645,856 describes the use of a carrier for hydrophobic drugs, including fenofibrate, and pharmaceutical compositions based thereon. The carrier comprises a digestible oil and a pharmaceutically-acceptable surfactant component for dispersing the oil in vivo upon administration of the carrier, which comprises a hydrophilic surfactant, said surfactant component being such as not to substantially inhibit the in vivo lipolysis of the digestible oil.

Sheu, M. T., et al, *Int. J. Pharm.* 103 (1994) 137–146, reported that a dispersion of fenofibrate in PVP still maintains the same crystalline form of the drug itself.

Palmieri, G. F., et al, *Pharma Sciences* 6 (1996) 188–194, reported that a dispersion of crystalline fenofibrate could be prepared in PEG 4000. However, dissolution of the composition was poor.

Gemfibrozil is another member of the fibrate class of lipid-regulating agents. U.S. Pat. No. 4,927,639 discloses a disintegratable formulation of gemfibrozil providing both immediate and sustained release, comprising a tablet compressed from a mixture of a first and second granulation, and a disintegration excipient operable to effect partial or complete disintegration in the stomach. The first granulation comprises finely divided particles of pure gemfibrozil granulated with at least one cellulose derivative, and the second granulation comprises finely divided particles of pure gemfibrozil granulated with a pharmaceutically-acceptable water soluble or insoluble polymer which are then uniformly coated with a pharmaceutically-acceptable (meth)acrylate copolymer prior to admixture with the first granulation. The first and second granulations are present in the final composition in a ratio of from about 10:1 to about 1:10.

U.S. Pat. No. 4,925,676 discloses a disintegratable gemfibrozil tablet providing both immediate and enteric release, which is compressed from a mixture of a first granulation of gemfibrozil with at least one acid-disintegratable binder, and a second granulation formed from the first granulation, but regranulated or coated with an alkali-disintegratable formulation of at least one substantially alkali-soluble and substantially acid-insoluble polymer.

Another class of lipid-regulating agents are commonly known as statins, of which pravastatin and atorvastatin are members. U.S. Pat. Nos. 5,030,447 and 5,180,589 describe stable pharmaceutical compositions, which when dispersed in water have a pH of at least 9, and include a medicament which is sensitive to a low pH environment, such as pravastatin, one or more fillers such as lactose and/or microcrystalline cellulose, one or more binders, such as microcrystalline cellulose (dry binder) or polyvinylpyrrolidone (wet binder), one or more disintegrating agents such as croscarmellose sodium, one or more lubricants such as magnesium stearate and one or more basifying agents such as magnesium oxide.

It is an object of the present invention to provide formulations of lipid-regulating agents having enhanced bioavailability when compared to commercially available formulations.

SUMMARY OF THE INVENTION

The present invention is directed to a process for preparing formulations comprising lipid-regulating agents with enhanced dissolution and absorption characteristics. More particularly, the process comprises dissolving the lipid-regulating agent in a supercritical fluid, spraying the supercritical fluid through a nozzle to form small particles comprising said lipid-regulating agent, forming a suspension of said lipid-regulating agent in a liquid in which the particles are insoluble and collecting said particles. The particles then be spray dried or lyophilized. They may optionally also be cooled with pharmaceutically-acceptable excipients, such as, for example, surfactants, polymers, lipids or other materials.

The resulting formulation results in an increase in drug solubility and oral bioavailability, and an improved dissolution rate.

The formulation may be administered directly, diluted into an appropriate vehicle for administration, encapsulated into hard gelatin capsules for administration, or administered by other means obvious to those skilled in the art.

DETAILED DESCRIPTION OF THE INVENTION

Figure 1:
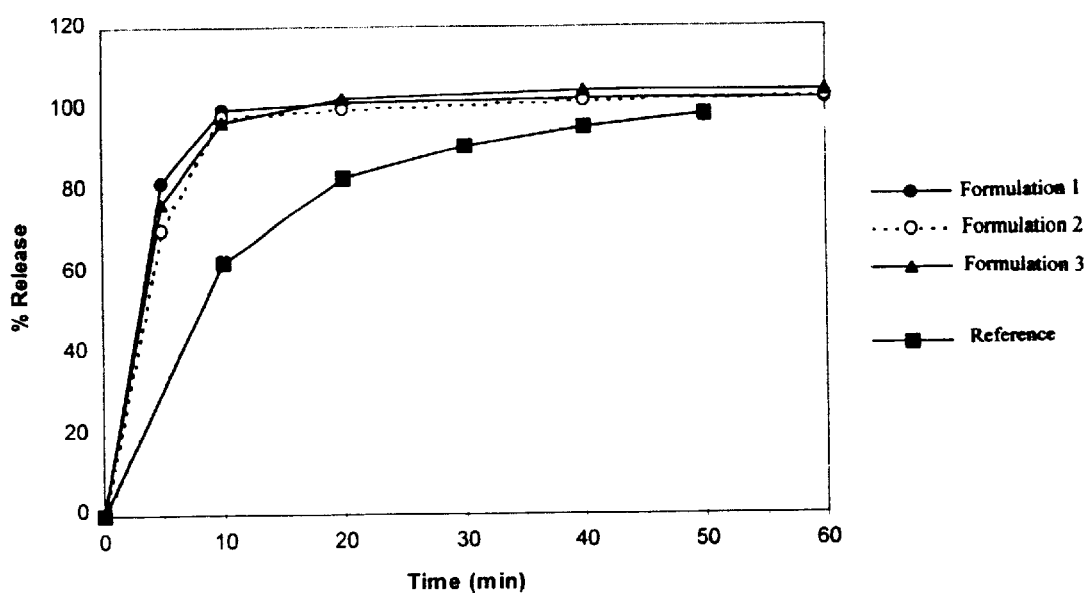
FIG. 1 is a graph showing the dissolution characteristics of fenofibrate nanocrystals or nanoparticles produced by the process of the present invention and reference compositions.

The bulk lipid-regulating agent may be prepared by any available method, as for example the compound fenofibrate may be prepared by the procedure disclosed in U.S. Pat. No. 4,058,552, or the procedure disclosed in U.S. Pat. No. 4,739,101, both herein incorporated by reference.

As used herein, the term "supercritical fluid" means a substance, such as for example carbon dioxide, which becomes a liquid state when its pressure and temperature are greater than its critical pressure and critical temperature, respectively.

As used herein, the term "nozzle" means a device through which a liquid is forced out under high pressure to become very fine (micronized) droplets.

The composition comprising the lipid-regulating agent may be prepared by using a SFX 220 supercritical particle generator, which consists of an ISCO extractor, controller, one or more D series syringe pumps, and a temperature controlled variable restrictor. The extractor incorporated six motor actuated valves that are controlled by the controller. The controller executes the process program and displays real-time data. The fluid source for the extractor is supplied by a unique syringe-type pump that maintains a constant process pressure in the extractor and up to the restrictor.

The lipid-regulating agent nanocrystals or nanoparticles are prepared by a process in which the drug is solubilized in the extractor at 50° C. and 2000 psi with carbon dioxide for a period of one to five minutes. The solutions are then released through a temperature controlled restrictor. Drug particles form when the carbon dioxide is. vaporized. Particle size can be controlled by varying the concentration of the solution and/or by the process flow rate.

Sub-micron particle size can be achieved either by using a very dilute solution or by adding additional liquid carbon dioxide through a second syringe pump to the outlet and before the restrictor.

Surface coating materials, such as phospholipids, surfactants, and/or polymers, may also be added either before or after particle formation to change properties of the surface of the sub-micron particles, as desired. The materials can be coated on the surface of these tiny particles in the process to become coated nanocrystals or nanoparticles, which can prevent from the growth or aggregation of particles. Representative particle size stabilizers include, for example, sodium lauryl sulfate (SLS) or sodium dodecylsufate (SDS) (BDH Laboratory Supplies), gelatin (Sigma), casein (Aldrich), lecithin (Sigma) and any phospholipids, gum acacia (TIC Gums), cholesterol (Aldrich), tragacanth (Sigma), stearic acid (Sigma), benzalkonium chloride (Sigma), calcium sterarate (Penta Manufacturing Company), glyceryl monostearate (ABITEC), cetostearyl alcohol (Croda), cetomarogol emulsifying wax (Croda), sorbitan esters (Uniqema), polyethylene glycols (Union Carbide), polyoxyethylene stearates (Uniqema), colloidal silicon dioxide (Cabot), phosphates (Sigma), caboxylmethylcellulose calcium (Kraft), carboxymethylcellulose sodium (Aldrich), methyl cellulose (Sigma), hydroxypropylmethycellulose phthaltate (Sigma), Microcrystalline cellulose (FMC), magnesium aluminum silicate (R. T. Vanderbilt), triethanolamine (Sigma), polyvinyl alcohol (Aldrich), PEG-2 stearate (Goldschmidt Chemical), PEG-stearate and gylcol stearate (Uniqema), PEG-6-32 stearate (Gattefosse), Gelucire 53/10 (Gattefosse), PEG-6 stearate (Protameen Chemicals), PEG-6 stearate and glyceryl stearate and ceteth-20 (Gattefosse), glyceryl stearate and PEG-75 stearate (Goldschmidt Chemical), hydrogenated palm oil/palm kernel oil PEG-6 complex (California Oils Corporation), glyceryl stearate and PEG-100 stearate (Uniqema), isoceteth-20 (Uniqema), PEG-6 sorbitan beeswax (Nikko Chemical), PEG 20 sorbitan beeswax (Nikko Chemical), Ceteth-10 (Protameen Chemicals), Cetech-20(Protameen Chemicals), Ceteareth-20 (Protameen Chemicals), Stearate-2 (Protameen Chemicals), Steareth-10 (Protameen Chemicals), Stearate-20 (Protameen Chemicals), stearate-100 (Uniqema), Pluronic F127 (BASF) and polyvinylpyrrolidone (BASF).

Other optional ingredients which may be included in the compositions of the present invention are those which are conventionally used in oil-based drug delivery systems, e.g. antioxidants such as tocopherol, tocopherol acetate, ascorbyl palmitate; ascorbic acid, butylhydroxytoluene, butylhydroxyanisole and propyl gallate; pH stabilisers such as citric acid, tartaric acid, fumaric acid, acetic acid, glycine, arginine, lysine and potassium hydrogen phosphate; thickeners/suspending agents such as hydrogenated vegetable oils, beeswax, colloidal silicon diocide, gums, celluloses, silicates, bentonite; flavouring agents such as cherry, lemon and aniseed flavours; sweeteners such as aspartame, saccharin and cyclamates; etc.

The particles comprising the lipid-regulating agent produced by the process of the present invention are preferable less than 5000 nm in diameter, more preferably less than 1000 nm in diameter.

The delivery system of the present invention results in an increased dissolution rate which improves bioavailability of the lipid-regulating agent.

The resulting composition comprising the lipid-regulating agent may be dosed directly for oral administration, diluted into an appropriate vehicle for oral administration, filled into hard gelatin capsules for oral administration, or delivered by some other means obvious to those skilled in the art. The said composition may be used to improve the dissolution rate, and the oral bioavailability, and increase the half-life of said lipid-regulating agent.

The invention will be understood more clearly from the following non-limiting representative examples:

EXAMPLE 1

Fenofibrate (100 mg) was added into a 10 mL cartridge in a critical fluid extractor. The cartridge was processed with 50 mL liquid carbon dioxide, which was heated and pressurized above its critical temperature and pressure. Fenofibrate was dissolved/finely dispersed in the supercritical carbon dioxide fluid. The outlet restrictor was adjusted to deliver the desire flow rate. The supercritical fluid containing solubilized/finely dispersed fenofibrate was filtered through a submicron pore sized filter, and then sprayed out through a nozzle. Liquid carbon dioxide became gas and submicron particles or nanoparticles dropped out. The particle size was determined using a API Particle Sizer. The particles may optionally be filled into capsules in a quantity appropriate to obtain the desired dose.

The equipment used in the experiment included:
 1. Isco Controller, Model SFX 200
 2. Isco Supercrtical Fluid Extractor, Model SFX 220
 3. Isco Syringe pump, Model 260D
 4. Isco Restrictor Temperature Controller
 5. Lauda Chiller, Model K2/RD
 6. Mettler Balcance, Model AE 100
 7. API Particle Sizer, Model Aerosizer LD The process parameters were:
Static Parameters:
 1. Time 1 minutes (range 1 to 10 minutes) (based on solubility)

2. Pressure 2000 psi
3. Temperature 50° C.

Dynamic Parameters:

1. Pressure 2000 psi
2. Temperature 50° C.
3. Time 10 minutes
4. Volume 50 mL
5. Flow rate 10 mL/min (range 1 to 20 mL/min)

EXAMPLE 2

Pravastatin 100 mg

Carbon dioxide (Liquid) 50 mL

Applying the general procedure of Example 1 one may obtain Pravastatin nanoparticles.

EXAMPLE 3

The method used in Example 1 to generate fenofibrate nanoparticles was limited to a small scale because of equipment capability.

The following formulations were used to generate larger quantity of fenonfibrate nanocrystals/nanoparticles using a milling process.

Formulations

| Formulation 1: | |
| --- | --- |
| Fenofibrate | 10 g |
| Sodium Lauryl Sulfate | 1 g |
| Formulation 2: | |
| Fenofibrate | 10 g |
| Pluronic F127 | 1 g |
| Formulation 3: | |
| Fenofibrate | 10 g |
| Gelucire 53/10 | 1 g |

These three formulations were prepared using three different particle size stabilizers—Sodium Lauryl Sulfate, Pluronic F127 and Gelucire 53/10. Each formulation was milled in water to the desire particle size and each suspension was filtered through a 1 micron filter to remove large particles. Each formulation was further processed using either a lyophilizing process or sprayed drying procedure to remove the milling media. The collected particles may optionally be filled into capsules in a quantity appropriate to obtain the desired dose.

The equipment used in the milling process including:

1. DYNO-MILL, model KDL
2. Peristaltic Pump
3. 0.6 L Jacked Glass Chamber
4. Lead Free Glass beads 0.5 mm (GlenMills Inc.)

The process parameters in the milling are listed below

| Mill Speed | 2000–4500 rpm |
| --- | --- |
| Temperature | 5–25° C. |
| Pump Rate | 20–200 ml/min |

EXAMPLE 4

A dissolution study was conducted to observe the dissolution rates of three types of nanoparticles/nanocrystal formulations generated in Example 3 and with that of a commercial formulation, Lipanthyl (Fournier SA). The results are illustrated in FIG. 1 below.

What is claimed is:

1. A process for preparing a nanocrystal or nanoparticle fibrate composition comprising the steps of dissolving a fibrate in a supercritical fluid, spraying the solution through a nozzle to form small particles of the fibrate, forming a suspension of the particles of said fibrate in a liquid, and collecting fibrate nanocrystal or nanoparticles.

2. A process of claim 1 wherein the supercritical fluid is carbon dioxide.

3. A process of claim 1 wherein the particle size of the fibrate agent is less than 5000 nm.

4. A process of claim 1 wherein the fibrate is fenofibrate.

5. A delivery system comprising a composition prepared by the process of claim 1.

6. A delivery system of claim 5 wherein said delivery system is a capsule.

7. A method of treating hyperlipidemia comprising administering a therapeutically-effective amount of a composition prepared by the process of claim 1 to a patient.

8. A method of treating hyperlipidemia comprising administering a therapeutically-effective amount of a composition prepared by the process of claim 4 to a patient.

9. A method of treating hyperlipidemia comprising administering a therapeutically-effective amount of a composition prepared by the process of claim 6 to a patient.

* * * * *